(12) United States Patent
Wong et al.

(10) Patent No.: US 7,516,644 B2
(45) Date of Patent: Apr. 14, 2009

(54) APPARATUS FOR TESTING BENDING STRENGTH

(75) Inventors: Shih-Fang Wong, Guangdong (CN);
Wen-Haw Tseng, Guangdong (CN);
Lei-Tong Yu, Guangdong (CN);
Xiu-Xuan Li, Guangdong (CN); Li Li,
Guangdong (CN); Yun-Tao Gao,
Guangdong (CN)

(73) Assignees: Hong Fu Jin Precision Industry (Shen Zhen) Co., Ltd., Longhua Town, Bao'an District, Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 28 days.

(21) Appl. No.: 11/612,479

(22) Filed: Dec. 19, 2006

(65) Prior Publication Data
US 2007/0193364 A1 Aug. 23, 2007

(30) Foreign Application Priority Data
Feb. 17, 2006 (CN) .................. 2006 1 0033808

(51) Int. Cl.
*G01N 3/30* (2006.01)

(52) U.S. Cl. .................. 73/12.07; 73/12.06; 73/849

(58) Field of Classification Search .............. 73/12.04, 73/12.07, 12.09, 12.12, 798, 816, 825, 849
See application file for complete search history.

(56) References Cited

U.S. PATENT DOCUMENTS

| | | | | | |
|---|---|---|---|---|---|
| 3,402,593 | A | * | 9/1968 | Bresk et al. | 73/12.07 |
| 3,485,083 | A | * | 12/1969 | Beal et al. | 73/12.07 |
| 3,600,932 | A | * | 8/1971 | Hill et al. | 73/12.07 |
| 4,426,683 | A | * | 1/1984 | Kissell | 700/275 |
| 5,686,652 | A | * | 11/1997 | Pfund | 73/12.04 |
| 6,976,387 | B2 | * | 12/2005 | Anthe et al. | 73/83 |
| 2004/0134263 | A1 | * | 7/2004 | Tsujii et al. | 73/81 |
| 2007/0209448 | A1 | * | 9/2007 | Wong et al. | 73/849 |

* cited by examiner

*Primary Examiner*—Harshad Patel
*Assistant Examiner*—Freddie Kirkland, III
(74) *Attorney, Agent, or Firm*—Winston Hsu

(57) ABSTRACT

An apparatus for testing bending strength is provided. The apparatus includes a frame, a load-supporting platform, a motor, and a control part. The load-supporting platform is mounted on the frame. The load-supporting platform includes a vessel configured for receiving a hand-held device. The motor includes a piston. A piston head is mounted on one end of the piston for impacting the vessel. The piston head includes a convex face oriented to face the vessel. The control part is configured for controlling the piston to move up and down repeatedly. The apparatus can be used to test a hand-held device's bending strength conveniently.

6 Claims, 3 Drawing Sheets

APPARATUS FOR TESTING BENDING STRENGTH

BACKGROUND

1. Technical Field

The present invention relates to an apparatus for testing bending strength, and particularly to an apparatus for testing hand-held device's bending strength.

2. General Background

Hand-held devices, such as mobile phones, media players, etc, are easily damaged by inadvertent pressing stress. For example, if the user sits down or squats down with the hand-held device is in the trousers' pocket of a user, the hand-held device will be subjected to the pressing stress. If the hand-held device is not strong enough, a liquid crystal display or an antenna of the hand-held device may be damaged.

For reasons mentioned above, after a hand-held device prototype is created, it is necessary to perform a bending strength test on the hand-held device prototype before the hand-held device is mass produced.

Therefore, what is needed is an apparatus for testing hand-held device' bending strength.

SUMMARY

An apparatus for testing bending strength is provided. The apparatus includes a frame, a load-supporting platform, a motor, and a control part. The load-supporting platform is mounted on the frame. The load-supporting platform defines a vessel configured for receiving a hand-held device. The motor includes a piston. A piston head is mounted on an end of the piston for impacting the vessel. The piston head includes a convex face oriented to face the vessel. The control part is for controlling the piston to move up and down repeatedly.

Other advantages and novel features will be drawn from the following detailed description with reference to the attached drawing, in which:

DETAILED DESCRIPTION OF THE EMBODIMENT

Figure 1:
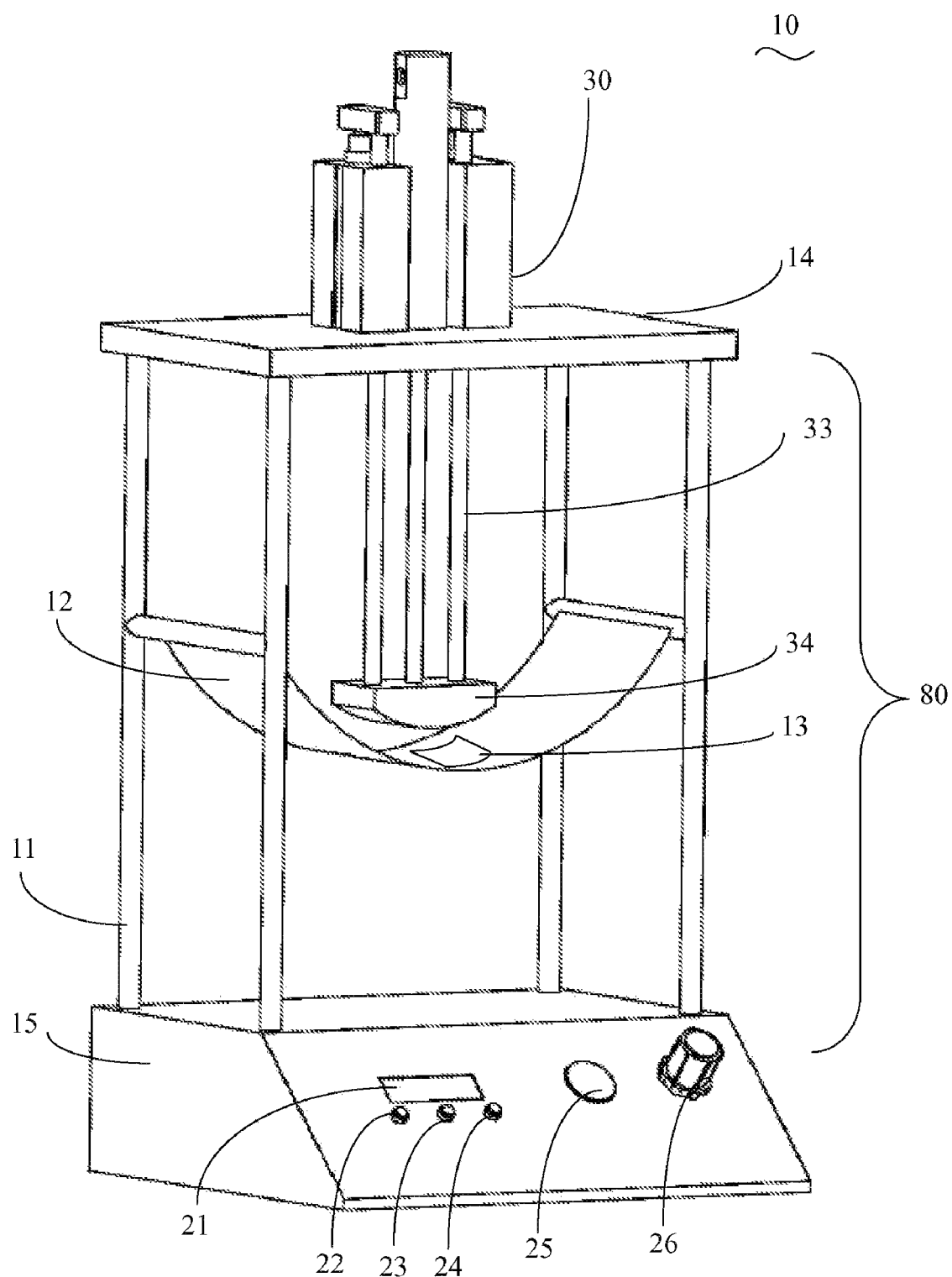
FIG. 1 is a schematic, solid view of an apparatus for testing bending strength according to a preferred embodiment of the present invention.
Figure 2:
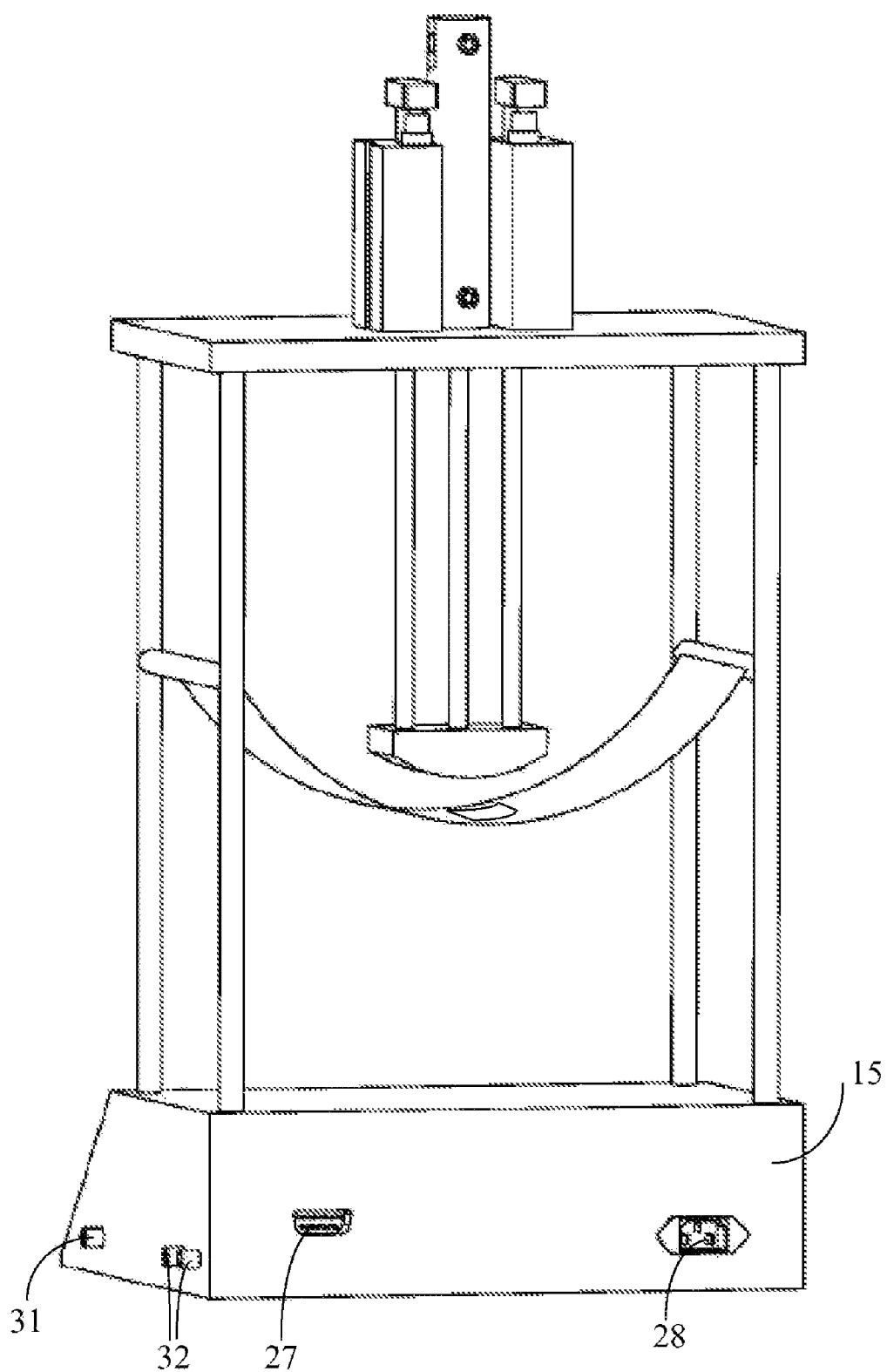
FIG. 2 is another schematic, solid view of the apparatus of FIG. 1.

Referring to FIGS. 1 and 2, an apparatus for testing bending strength is disclosed. The apparatus 10 includes a frame 80 and a motor 30. The frame 80 includes a base 15, a plurality of support beams 11, and a platform 14. In the embodiment of the present invention, the motor 30 is a pneumatic actuator. The pneumatic actuator 30 is mounted on the platform 14. A piston 33 of the pneumatic actuator 30 is constructed with three arms. A piston head 34 is mounted on an end of the three arms of the piston 33. The piston head 34 has a face slightly curved outwardly. A load-supporting platform 12 is mounted on the beams 11. The load-supporting platform 12 includes a vessel 13. The vessel 13 is configured for receiving a hand-held device. The load-supporting platform 12 and the vessel 13 are curved. The curved face of the piston head 34 is oriented to face the vessel 13.

An intake duct 31, two exhaust ducts 32, a manometer 25, and a regulator knob 26 are mounted on the base 15. The intake duct 31 and the exhaust ducts 32 are connected to an air pump (not shown). The manometer 25 shows an air pressure of the pneumatic actuator 30. The regulator knob 26 regulates the air pressure in the pneumatic actuator 30. A display 21, input keys (e.g., an "enter" input key 22, an "up" input key 23, and a "down" input key 24), a power socket 28, and a communication port 27 are also positioned on the base 15. The display 21 shows parameters of the apparatus 10 (e.g., a target number of impacts, a impact frequency), and a test status (e.g., a number of impacts). The power socket 28 is used for connecting to a power supply (not shown). The communication port 27 can be an RS232 port. The communication port 27 is used to connect the apparatus 10 to a computer so as to transfer data between the apparatus and the computer. Data transfers include receiving control instructions from the computer.

Figure 3:
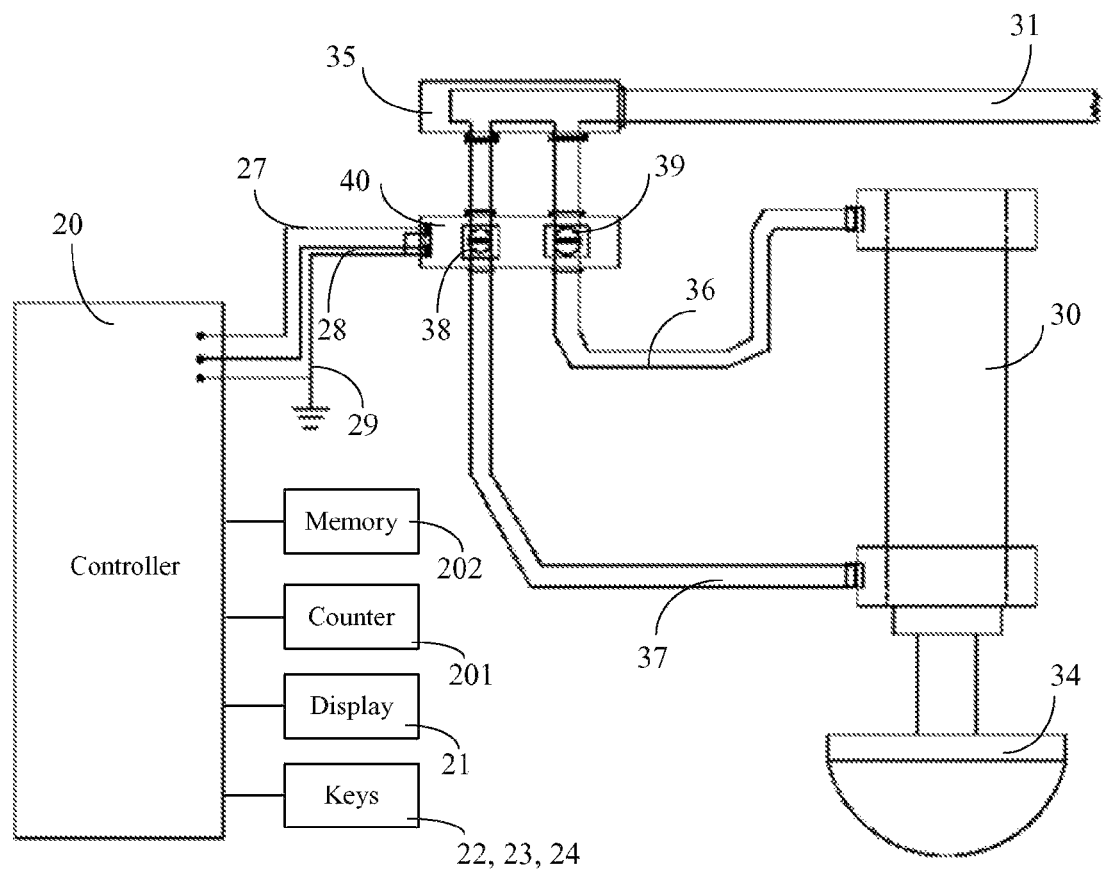
FIG. 3 is a schematic diagram of a hardware infrastructure of the apparatus of FIG.

Referring to FIG. 3, a hardware infrastructure of the apparatus 10 is disclosed. A controller 20 and a valve controller 40 are positioned in the base 15. The controller 20 and the valve controller 40 control the pneumatic actuator 30, thus, driving the piston 33 to move up and down repeatedly. The controller 20 and the valve controller 40 are connected by three separate control wires 27, 28, 29. The control wire 29 further connects to earth. The valve controller 40 includes two valve switches 38, 39. Each of the valve switch 38 and the valve switch 39 is independently opened and closed by the controller. When the valve switch 38 is opened, Air flows into the intake duct 31, a slide valve 35, the air pipe 37, and a first cylinder of the pneumatic actuator 30, retracting the piston head 34 up. If the valve switch 39 is opened, Air flows into the intake duct 31, the slide valve 35, the air pipe 36, and a second cylinder of the pneumatic actuator 30, driving the piston head 34 outwards. When the valve switch 38/39 is closed, air in the pneumatic actuator 30 exhausts through the exhaust pipe 32. When the valve switches 38/39 are opened alternatively, the piston head 34 moves up and down repeatedly. The regulator knob 26 controls air pressure of the cylinders of the pneumatic actuator 30 through the valve controller 40, so as to control an impact power of the piston head 34.

The controller 20 is further connected to a memory 202, a counter 201, the display 21, and the input keys 22, 23, 24. The counter 201 includes a counter reset mechanism to start a count at zero. The counter 201 counts the number of impacts of the piston head 34 on the vessel 13. The memory 202 stores programs and parameters. The programs include an impact-executing program, and a parameter-setting program. The parameters include the impact frequency, and the target number of impacts. The input keys 22, 23, 24 are used to start or stop the impact-executing program and to set the parameters. If the impact-executing program is executed, the controller 20 controls the piston head 34 to move up and down repeatedly until the number of impacts equals to the target number of impacts or when a stop command is received from the input keys 22, 23, 24.

Although the present invention has been specifically described on the basis of a preferred embodiment and preferred method thereof, the invention is not to be construed as being limited thereto. Various changes or modifications may be made to the embodiment and method without departing from the scope and spirit of the invention.

What is claimed is:

1. An apparatus for testing bending strength, comprising:
   a frame;
   a load-supporting platform mounted on the frame, wherein the load-supporting platform comprises a vessel configured for receiving a hand-held device, the load-supporting platform and the vessel are curved;
   a motor comprising a piston and an piston head, wherein the piston head is mounted on one end of the piston for impacting the vessel, the piston head comprises a face oriented to face the vessel, the face is slightly curved outwardly; and
   a control part for controlling the piston to move up and down repeatedly.

2. The apparatus of claim 1, wherein the motor is a pneumatic actuator.

3. The apparatus of claim 2, wherein the control part comprises a controller and a valve controller, and the controller controls the valve controller to open or close.

4. The apparatus of claim 1, further comprising input keys for setting parameters or starting/stopping a test.

5. The apparatus of claim 1, further comprising a display for showing a test result or parameters.

6. The apparatus of claim 1, further comprising a communication port configured for communicating with an external computer.

* * * * *